United States Patent [19]

Kitamura et al.

[11] Patent Number: 5,152,919

[45] Date of Patent: Oct. 6, 1992

[54] OPTICALLY ACTIVE COMPOUNDS, LIQUID CRYSTAL COMPOSITIONS COMPRISING SAID COMPOUNDS, AND LIQUID CRYSTAL OPTICAL MODULATORS USING SAID COMPOSITIONS

[75] Inventors: Teruo Kitamura; Katsumi Kondo; Yuka Sudo, all of Ibaraki; Koichi Matsumura, Osaka; Mitsuru Kawada, Hyogo; Yoshihiro Sugihara, Osaka, all of Japan

[73] Assignees: Hitachi, Ltd., Tokyo; Takeda Chemical Industries, Ltd., Osaka, both of Japan

[21] Appl. No.: 497,269

[22] Filed: Mar. 22, 1990

[30] Foreign Application Priority Data

Mar. 22, 1989 [JP]   Japan .................................. 1-67561

[51] Int. Cl.$^5$ ...................... C09K 19/34; C09K 19/20; C09K 19/12; C07D 239/02
[52] U.S. Cl. ........................... 252/299.61; 252/299.64; 252/299.65; 252/299.66; 252/299.67; 544/335
[58] Field of Search ...................... 252/299.01, 299.61, 252/299.64, 299.65, 299.66, 299.67; 544/298, 335

[56] References Cited

U.S. PATENT DOCUMENTS

| | | | |
|---|---|---|---|
| 4,954,600 | 9/1990 | Hachiya | 528/89 |
| 4,959,173 | 9/1990 | Shibata et al. | 252/299.65 |
| 4,980,083 | 12/1990 | Shibata et al. | 252/299.61 |

FOREIGN PATENT DOCUMENTS

| | | |
|---|---|---|
| 0174816 | 3/1986 | European Pat. Off. . |
| 0322862 | 7/1989 | European Pat. Off. . |
| 86/04328 | 7/1986 | World Int. Prop. O. . |

Primary Examiner—Robert L. Stoll
Assistant Examiner—Shean C. Wu
Attorney, Agent, or Firm—Antonelli, Terry, Stout & Kraus

[57] ABSTRACT

The present invention discloses dichiral compounds represented by the general formula

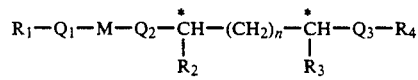

($R_1$, $R_2$, $R_3$, $R_4$, $Q_1$, $Q_2$, $Q_3$, M and n have the same definitions as in the description portion of the specification), intermediates for preparation of said compounds, liquid crystal compositions comprising said compounds, and liquid crystal optical modulators using said compositions.

9 Claims, 1 Drawing Sheet

OPTICALLY ACTIVE COMPOUNDS, LIQUID CRYSTAL COMPOSITIONS COMPRISING SAID COMPOUNDS, AND LIQUID CRYSTAL OPTICAL MODULATORS USING SAID COMPOSITIONS

BACKGROUND OF THE INVENTION

1. Field of the Invention

The present invention relates to optically active compounds and liquid crystal compositions comprising said compounds. The compounds and compositions of the present invention show a ferroelectric liquid crystal phase, and accordingly are useful as electrooptic switching elements (e.g. liquid crystal display devices) and can be applied to liquid crystal optical modulators.

2. Related Art

Liquid crystal display devices have various excellent features such as low-voltage operability, lower electricity consumption, being thin and light-weight, being a non-emissive type and easy on the eye, etc. Accordingly, they are in wide use as various display devices. Liquid crystal display devices using a nematic liquid crystal operating in the so-called twisted nematic mode (TN mode) are in use currently. However, the display devices using this nematic liquid crystal have the drawback of being very slow in response as compared to luminescent type display devices such as CRT, EL and the like. Accordingly, when the liquid crystal display devices using a nematic liquid crystal are applied in a large-scale display device capable of displaying a large amount of information, it is impossible to obtain a display of good contrast because of insufficient threshold characteristic. Thus, the liquid crystal display devices using a nematic liquid crystal have had a limitation for wide application. There has recently been developed a liquid crystal display device using a nematic liquid crystal operating in the so-called super twisted nematic mode (STN mode) or SBE and capable of giving a display of improved contrast because of improved threshold characteristic. Even in this STN mode liquid crystal display device, however, the response is not significantly improved, and therefore said device has a limitation for application to displays capable of displaying a still larger amount of information. Hence, various attempts have been made to develop a new liquid crystal display system capable of giving excellent response.

Ferroelectric liquid crystals have a memory characteristic and give a high speed response, and accordingly their application to large-scale displays is highly expected. As liquid crystals having ferroelectric properties, there are known those showing a chiral smectic C phase, a chiral smectic H phase, a chiral smectic J phase, etc.

Of these ferroelectric liquid crystals, those showing a chiral smectic C phase were first synthesized in 1975 by R. B. Meyer et al.; one typical example thereof is 2-methylbutyl 4-(4'-decyloxybenzylideneamino)cinnamate (hereinafter abbreviated to DOBAMBC) [J. Physique, 36, L-69 (1975)].

A thin film liquid crystal cell was prepared using DOBAMBC and was found to have a high speed response in the order of $\mu$sec [N. A. Clark et al., Appl. Phys. Lett., 36, 89 (1980)]. Since that time, there was started the development of optical modulation devices (e.g. liquid crystal display devices, photo-printer heads) using a ferroelectric liquid crystal showing a chiral smectic C phase (hereinafter may be referred to simply as "ferroelectric liquid crystal").

As a result, a number of ferroelectric liquid crystal compounds showing a chiral smectic C phase have been developed since then, and various ferroelectric liquid crystal compounds are already known. However, no ferroelectric liquid crystal compound is found yet which has satisfactory reliability and capability for use in large-scale displays, etc.

In order for a ferroelectric liquid crystal to be practically used in a liquid crystal display device, etc., the liquid crystal must be superior in high speed response, orientation, memory characteristic, characteristic of threshold voltage, temperature dependences of these properties, etc. Also, the ferroelectric liquid crystal is required to show a chiral smectic C phase over a wide temperature range so that it can operate within a sufficiently wide temperature range including room temperature, and further to have excellent physical and chemical stabilities.

Of these requirements, particularly important are physical and chemical stabilities, high speed response, large spontaneous polarization necessary for the expression of memory characteristic, large pitch of cholesteric structure for achieving good orientation, and wide temperature range shown by chiral smectic C phase.

None of the so far developed ferroelectric liquid crystal compounds satisfy almost all of the above requirements. For example, the above-mentioned DOBAMBC, being a SCHIFF's base type liquid crystal, has a problem in chemical stability to water, light, etc. and moreover is low in spontaneous polarization (4 $nC/cm^2$ or less).

Ester type liquid crystals have been reported as a chemically stable ferroelectric liquid crystal compound. These liquid crystals, however, are not satisfactory because they neither have a sufficiently large spontaneous polarization nor a sufficiently wide temperature range for chiral smectic C phase.

In order to obtain a larger spontaneous polarization, there have been synthesized compounds having two asymmetric carbon atoms in the optically active group which is essential for the expression of chiral smectic C phase.

These compounds include, for example, liquid crystal compounds having a dichiral epoxide side chain [David M. Walba et al., Journal of American Chemical Society, 108, 7424 (1986)], and liquid crystal compounds having a halogen atom and a methyl group on two adjacent asymmetric carbon atoms [cf. e.g. JP-A-168780/1985, 218358/1985, 68449/1986, 40/1987, 46/1987, 103043/1987, 111950/1987, 142131/1987, 175443/1987].

A typical example of the above liquid crystal compounds is 4'-octylcarbonyloxy-4-biphenyl (S)-3-methyl-2-chloropentanoate [JP-A-68449/1986]. This liquid crystal compound has a very large spontaneous polarization of 190 $nC/cm^2$, but, being an aliphatic chloro compound, has poor chemical stability. Hence, there has been synthesized 4'-octylcarbonyloxy-4-[(S)-2-methoxy-(S)-3-methylpentyloxycarbonyl]biphenyl [JP-A228036/1987]. This compound has excellent chemical stability but has a small spontaneous polarization of 17 $nC/cm^2$.

As described above, according to the prior art there has been found yet no ferroelectric liquid crystal compound which satisfies requirements such as physical and chemical stabilities, high speed response, large spontaneous polarization (necessary for the expression of memory characteristic) and the like.

OBJECT AND SUMMARY OF THE INVENTION

The object of the present invention is to provide a ferroelectric liquid crystal compound which satisfies requirements when applied to liquid crystal devices, such as physical and chemical stabilities, high speed response, large spontaneous polarization (necessary for the expression of memory characteristic), large pitch of cholesteric structure (necessary for obtaining good orientation), and wide temperature range shown by chiral smectic C phase.

In order to achieve the above object, the present inventors made in-depth investigation on the correlation of (a) chemical structure of liquid crystal molecule and (b) physical and chemical stabilities, spontaneous polarization, cholesteric pitch and temperature range of chiral smectic C phase, of the liquid crystal. As a result, the present invention has been found. That is study on liquid crystal compounds obtained by combining a chemically stable ester compound and an optically active group having two asymmetric carbon atoms has led to the completion of the present invention. Specifically, it was found that the pattern of bonding between two asymmetric carbon atoms and the 6-membered ring (e.g. benzene) constituting the skeleton of liquid crystal compound has a close connection to the spontaneous polarization and temperature range shown by chiral smectic C phase, of the liquid crystal compound and further that when the two asymmetric carbon atoms are linked via a chain of a plurality of methylene groups, the control of cholesteric pitch becomes possible. These findings have achieved the above object.

DETAILED DESCRIPTION OF PREFERRED EMBODIMENTS

Figure 1:
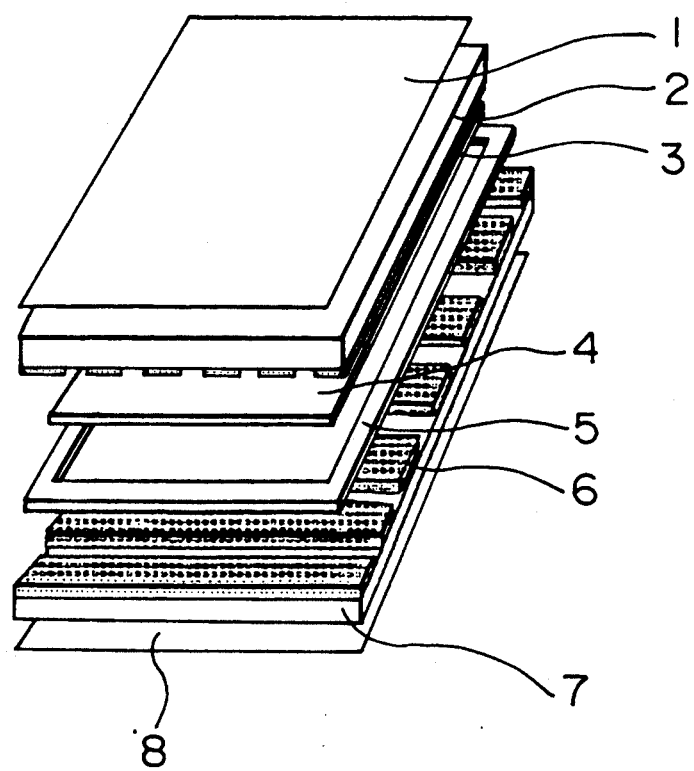
FIG. 1 is a schematic illustration of an example of the liquid crystal display device according to the present invention. 1 and 8 are each a polarization plate; 2 is a front side glass; 3 and 6 are each a transparent electrode; 4 is a ferroelectric liquid crystal phase; 5 is a seal; 7 is a back side glass.

One aspect of the present invention relates to optically active compounds represented by the general formula

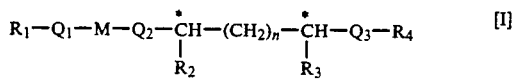

[I]

wherein $R_1$ is an alkyl group or an alkenyl group each of 3-14 carbon atoms; $R_2$ and $R_3$ are independently a lower alkyl group of 1-3 carbon atoms; $R_4$ is an alkyl group of 1-10 carbon atoms; $Q_1$, $Q_2$ and $Q_3$ are independently a single bond, a (thio)ether group, a (thio)carboxylic acid ester group, a carbonyl group or a carbonyldioxy group; n is an integer of 2-6; M is

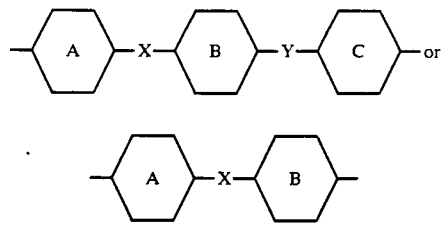

(X and Y are independently a single bond, a (thio)carboxylic acid ester group, a methyleneoxy group or an ethylene group, and

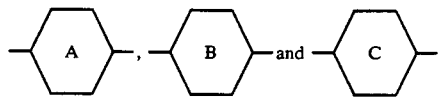

are independently a six-membered ring-1,4-diyl group which may contain 1-2 oxygen or nitrogen atoms as ring-forming atoms); the carbon atoms with the asterisk (*) denote asymmetric carbon atoms, as well as to liquid crystal compositions comprising at least one of said optically active compounds.

Other aspect of the present invention relates to liquid crystal optical modulators using one of said liquid crystal compositions.

The compounds I can be classified into the following compounds I' and I'', depending upon the basic skeleton M.

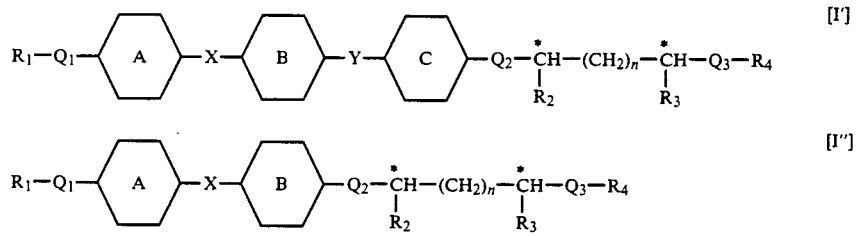

In the above compounds I, I' and I'', the alkyl groups of 3-14 carbon atoms, represented by $R_1$ can be of straight chain or branched chain. Specifically, there can be mentioned straight chain alkyl groups such as propyl, butyl, pentyl, hexyl, heptyl, octyl, nonyl, decyl, undecyl, dodecyl, tridecyl, tetradecyl and the like, as well as branched chain alkyl groups such as isopropyl, isobutyl, sec-butyl, tert-butyl, isopentyl, neopentyl, tert-pentyl, isohexyl, 1-methylpentyl, 2-methylpentyl, 5-methylhexyl, 2,3,5-trimethylhexyl, 2,7,8-trimethyldecyl, 4-ethyl-5-methylnonyl and the like. Of these, preferable are straight chain alkyl groups of 6-12 carbon atoms, such as hexyl, heptyl, octyl, decyl, undecyl, dodecyl and the like.

The alkenyl group of 3-14 carbon atoms can be of straight chain or branched chain. Specifically, there can be mentioned straight chain alkenyl groups such as propenyl, butenyl, pentenyl, hexenyl, heptenyl, octenyl, nonenyl, decenyl, undecenyl, dodecenyl, tridecenyl, tetradecenyl and the like, as well as branched chain alkenyl groups such as isopropenyl, isoallyl (isobutenyl), sec-butenyl, tert-butenyl, isopentenyl, tert pentenyl, isohexenyl, 1-methylpentenyl and the like. Of these, preferably are straight chain alkeny groups of 6-12 carbon atoms, such as hexenyl, heptenyl, octenyl, decenyl, undecenyl, dodecenyl and the like.

As the lower alkyl group of 1-3 carbon atoms, represented by $R_2$ and $R_3$, there can be mentioned straight chain or branched chain alkyl groups such as methyl, ethyl, propyl, isopropyl and the like. Of these, methyl is preferable.

The alkyl groups of 1-10 carbon atoms represented by $R_4$ can be of straight chain or branched chain. Specifically, there can be mentioned straight chain alkyl groups such as methyl, ethyl, propyl, butyl, pentyl, hexyl, heptyl, octyl, nonyl, decyl and the like, as well as branched chain alkyl groups such as isopropyl, isobutyl, sec-butyl, tert-butyl, isopentyl, neopentyl, tert-pentyl, isohexyl, 1-methylpentyl, 2-methylpentyl, 5-methylhexyl, 4-ethylhexyl, 2,3,5-trimethylhexyl, 4-ethyl-5-methylhexyl and the like. Of these, preferable are straight chain alkyl groups of 1-8 carbon atoms, such as methyl, ethyl, propyl, butyl, pentyl, hexyl, heptyl and octyl.

As the (thio)carboxylic acid ester group represented by $Q_1$, $Q_2$ and $Q_3$, there can be mentioned a

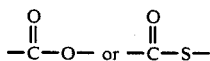

ester group and a

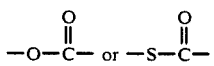

ester group.

With respect to the various bond and groups which can be taken by $Q_1$, $Q_2$ and $Q_3$, $Q_1$ is preferably a single bond, a (thio)ether group or a

ester group; $Q_2$ is preferably a

ester group, a

ester group or a (thio)ether group; and $Q_3$ is preferably a (thio)ether group, a

ester group or a

ester group.

As the (thio)carboxylic acid ester group represented by X and Y, there can be mentioned a

ester group and a

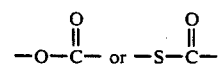

ester group. As the methylenoxy group represented by X and Y, there can be mentioned a —CH$_2$O— group and a —OCH$_2$— group.

As the six-membered ring-1,4-diyl group represented by

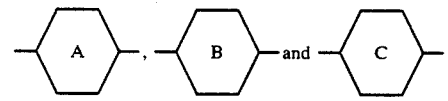

there can be specifically mentioned, for example, p-phenylene, 1,4-cyclohexylene, 2,5-(1,3-dioxane)diyl, 2,5-pyridinediyl, 2,5-pyrimidinediyl, 2,5-(1,4-pyrazine)diyl and 3,6-(1,2-pyridazine)diyl. These rings may be substituted with halogen, cyano, methyl or methoxy.

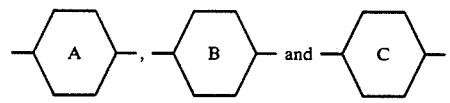

may be the same or different.

2,5-(1,3-Dioxane)diyl can be

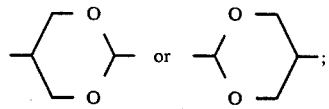

2,5-pyridinediyl can be

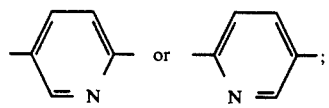

2,5-pyrimidinediyl can be

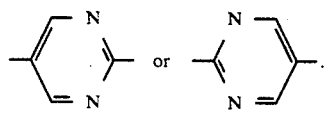

When M is

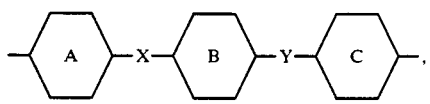

preferable combinations of

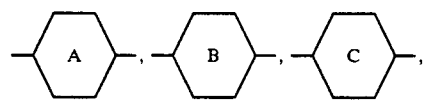

X and Y include a case where one of X and Y is a single bond, the other of them is a (thio)carboxylic acid ester bond, and all of

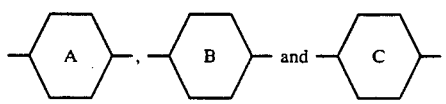

are p-phenylene or one of them is 2,5-pyrimidinediyl. When M is

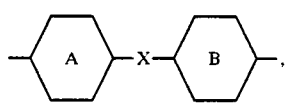

preferable combinations of

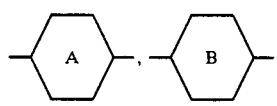

and X include a case where X is a single bond and both of

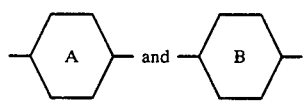

are p-phenylene or one of them is 2,5-pyrimidinediyl.

The compounds I have two asymmetric carbon atoms within the molecule and therefore have four different optical isomers, that is, (R,R) type, (R,S) type, (S,R) type and (S,S) type.

The compounds I of the present invention can be produced according to, for example, the following processes.

Process 1

Compounds of the general formula I wherein $Q_2$ is a

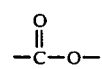

ester group.

Scheme 1

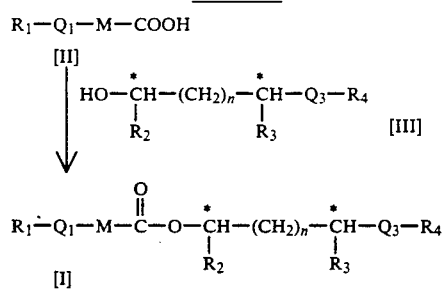

($R_1$ to $R_4$, $Q_1$, $Q_3$ and M have the same definitions as above. The same applies hereinafter.)

As shown in the above scheme 1, the compound I can be obtained by subjecting a carboxylic acid II and an optically active dichiral alcohol III to a condensation reaction. This condensation reaction per se is known and can be effected according to a conventional method. For example, the carboxylic acid II and the dichiral alcohol III are condensed in an organic solvent in the presence of a proton acid. As the proton acid, there can be used, for example, inorganic acids such as sulfuric acid, hydrochloric acid, perchloric acid and the like; organic sulfonic acids such as p-toluene-sulfonic acid, benzenesulfonic acid, trifluoromethane-sulfonic acid, methanesulfonic acid and the like; and strongly acidic ion exchange resins such as Amberlist ® and the like. The carboxylic acid II can be replaced by a thiocarboxylic acid; in that case, the condensation reaction with the dichiral alcohol III can be effected in the same manner. As the organic solvent, there can be mentioned, for example, hydrocarbons such as hexane, benzene, toluene and the like; halogenated hydrocarbons such as chloroform, methylene chloride, carbon tetrachloride, 1,2-dichloroethane and the like; ethers such as diethyl ether, tetrahydrofuran, dioxane and the like; ethyl acetate; acetonitrile; and dimethylformamide. It is possible that the carboxylic acid II be converted to an acid halide with, for example, a halogenating agent such as phosphorus pentachloride, thionyl chloride, thionyl bromide or the like and the halide be reacted with the dichiral alcohol III in the above mentioned organic solvent in the presence of, for example, a tertiary amine such as pyridine, triethylamine or the like. It is further possible that the alcohol III be converted to a trimethylsilyl ether derivative

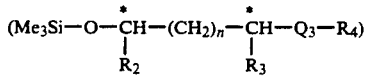

and the ether be condensed with an acid halide derivative of the carboxylic acid II in the presence of Lewis acid such as zinc chloride or the like. This applies also when a this carboxylic acid is used in place of the carboxylic acid II.

It is furthermore possible that the carboxylic acid II and the alcohol III be reacted with an activating agent such as N,N'-dicyclohexylcarbodiimide (DCC), Mukaiyama's reagent illustrated by a 1-methyl-2-halopyridium iodide, diethyl azodicarboxylate (DEAD) and triphenylphosphine (Ph₃P) (Mitsunobu's reagent), triphenylphosphine dibromide or the like.

These methods are described in, for example, J. Org. Chem., 27, 4675 (1962); Tetrahedron Lett., 1978, 4475; Chemistry Lett., 1975, 1045; Chemistry Lett., 1976, 13; Bull. Chem. Soc. Japan 50, 1863 (1977); Bull, Chem. Soc. Japan. 40, 2380 (1967); Syn. Commun., 16, 1423 (1986); and Syn. Commun., 16, 659 (1986).

Process 2

Compounds of the general formula I wherein $Q_2$ is a

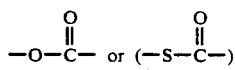

ester group.

Scheme 2

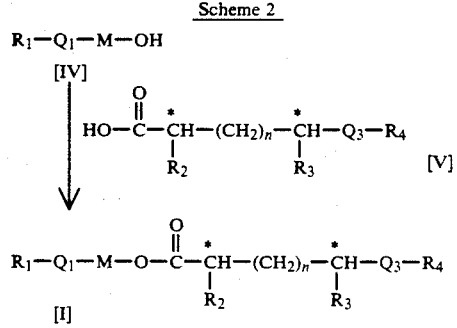

As shown in the above scheme 2, the compound I can be obtained by subjecting a hydroxyl group-containing compound IV and an optically active dichiral carboxylic acid V to a condensation reaction. This condensation reaction per se is known and can be effected according to a conventional method as mentioned above. The carboxylic acid V can be replaced by an optically active dichiral thiocarboxylic acid; in that case, the condensation reaction with the compound IV can be effected in the same manner.

Process 3

Compounds of the general formula I wherein $Q_2$ is a (thio)ether group (—O— or —S—)

Scheme 3

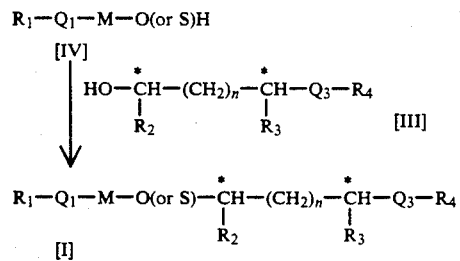

As shown in the above scheme 3, the compound I can be obtained by subjecting a hydroxyl or thiol group-containing compound IV and an optically active dichiral alcohol III to an etherification reaction. This etherification reaction per se is known and can be effected according to a conventional method. For example, the reaction can be effected with diethyl azodicarboxylate (DEAD) and triphenylphosphine ($Ph_3P$) (S. Bittner et al., Chem. & Ind., 1975, 281).

It is also possible that the dichiral alcohol III and an organic sulfonyl chloride be reacted in an organic solvent in the presence of an organic base (e.g. pyridine, triethylamine) or an inorganic base (e.g. sodium hydride) to obtain a corresponding organic sulfonic acid ester and the ester be reacted with the hydroxyl or thiol group containing compound IV. This reaction is conducted in an organic solvent in the presence of an inorganic base (e.g. potassium carbonate, sodium hydride) or an organic base (e.g. pyridine, triethylamine). As the organic sulfonyl chloride usable in the reaction, there can be mentioned, for example, aromatic sulfonyl chlorides such as p-toluenesulfonyl chloride, o-toluenesulfonyl chloride, p-chlorobenzenesulfonyl chloride, benzenesulfonyl chloride, α-naphthalenesulfonyl chloride, β-naphthalenesulfonyl chloride and the like, as well as aliphatic sulfonyl chlorides such as methanesulfonyl chloride, trifluoromethanesulfonyl chloride and the like.

As the organic solvent usable in the etherification reaction, there can be mentioned, for example, aliphatic hydrocarbons (e.g. hexane, cyclohexane), halogenated hydrocarbons (e.g. chloroform, methylene chloride, carbon tetrachloride, 1,2-dichloroethane), ethers (e.g. diethyl ether, tetrahydrofuran, dioxane), aromatic hydrocarbons (e.g. benzene, toluene), ethyl acetate, acetonitrile, dimethylformamide (DMF), dimethyl sulfoxide (DMSO) and hexamethylphosphoric triamide (HMPA).

In the etherification reaction, the activation of the dichiral alcohol III can be effected not only by converting the dichiral alcohol III to the above mentioned organic sulfonic acid ester but also by converting the alcohol III to a halogen derivative. The conversion to a halogen derivative can be effected by, for example, reacting the organic sulfonic acid ester with a metal halide (e.g. sodium iodide, potassium iodide). Or, the dichiral alcohol III can be directly reacted with a halogenating agent such as phosphorus pentachloride, thionyl chloride, thionyl bromide or the like. The thus obtained halogen derivative can be reacted with the hydroxyl group-containing compound IV in an organic solvent in the presence of the above mentioned inorganic or organic base.

The compounds I obtained by the above processes can be separated from the reaction mixture and purified by conventional separation and purification methods such as extraction, solvent operation, column chromatography, liquid chromatography, recrystallization and the like.

All of the starting materials II, III, IV and V for production of the optically active compounds I of the present invention are known substances or can be easily derived from known substances. For example, the optically active dichiral compound III or V represented by the general formula given later can be derived from known optically active dichiral compounds, and can also be obtained by, for example, a chemical asymmetric synthesis [J. D. Morrison et al., Asymmetric Synthesis, vol. 1 (1983) to vol. 5 (1985); B. Bosnich et al., Asymmetric Catalysis (1986); M. A. Sutter et al., Ann., 1983, 939], a biological asymmetric synthesis using an enzyme or a microorganism [J. B. Jones et al., "Applications of Biochemical Systems in Organic Chemistry", John Wiley, New York (1976); G. Frater et al., Tetrahedron, 40, 1269 (1984); R. W. Hoffman et al., Chem. Ber., 11, 2786 (1981); K. Nakamura et al., Tetrahedron Lett., 27, 3155 (1986)], and an optical resolution [J. Jacques et al., "Enantiomers, Racemates and Resolutions", John Wiley & Sons (1981); A. W. Ingersoll, Org. Synth., Coll. vol., 2, 506 (1943); H. Nohira et al., Chemistry Lett., 1981, 875, 951].

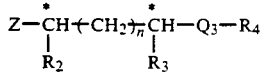

[$Q_3$, $R_2$, $R_3$ and $R_4$ have the same definitions as above; Z is a hydroxyl or thiol group (the case of a compound III), or a carboxyl group (the case of a compound V).] The thus obtained dichiral compound III or V can be subjected to inversion of configuration on asymmetric carbon by a chemical or biological method to convert it into other optical isomer(s). As the typical methods for inverting the hydroxyl group of optically active secondary alcohol, there are known, for example, a method in which the hydroxyl group is converted into a corresponding organic sulfonic acid ester and then subjected to an intramolecular nucleophillic substitution reaction to effect inversion [E. J. Corey et al., Tetrahedron Lett., 1975, 3183; D. T. Sawyer and M. J. Gibian, Tetrahedron, 35, 1471 (1979); W. H. Kruizinga et al., J. Org. Chem., 46, 4321 (1981); J. W. Hoffman and R. C. Desai, Syn. Commun., 13, 553 (1978)], a method in which an optically active secondary alcohol is activated by N,N'-dicyclohexylcarbodiimide (DCC) in the presence of cuprous chloride and then reacted with an appropriate carboxylic acid to effect inversion [J. kaulen, Angew. Chem., 99, 800 (1987)], and a method in which an optically active secondary alcohol is reacted with diethyl azodicarboxylate (DEAD), triphenylphosphine ($Ph_3P$) and an appropriate carboxylic acid to effect inversion [O. Mitsunobu and E. Eguchi, Bull. Chem. Soc. Japan, 44, 3427 (1971); O. Mitsunobu, Synthesis, 1981, 1].

Next, there are described typical examples of the optically active dichiral secondary alcohol III and the optically active dichiral carboxylic acid V which are both important materials for formation of the dichiral portion of the optically active compounds of the present invention. Firstly, there are shown specific examples of the optically active compounds III and V wherein n=2.

A. Optically active dichiral secondary alcohols III (1) $Q_3$=ether group, $R_2$=$R_3$=methyl group

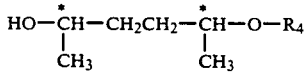

When $R_4$ is a $C_{1-10}$ alkyl group, that is, when the above formula is a 5-alkyloxy-2-hexanol, its specific examples include 5-methoxy-2-hexanol, 5-ethoxy-2-hexanol, 5-propoxy-2-hexanol, 5-butoxy-2-hexanol, 5-pentyloxy-2-hexanol, 5-hexyloxy-2-hexanol, 5-heptyloxy-2-hexanol, 5-octyloxy-2-hexanol, 5-nonyloxy-2-hexanol, 5-decyloxy-2-hexanol, 5-isopropoxy-2-hexanol, 5-isobutoxy-2-hexanol, 5-tert-butoxy-2-hexanol, 5-(2-methylpentyloxy)-2-hexanol and 5-(3-methylpentyloxy)-2-hexanol.

(2) $Q_3$=

ester group, $R_2$=$R_3$=methyl group

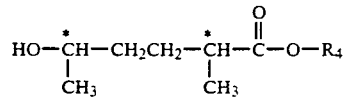

When $R_4$ is a $C_{1-10}$ alkyl group, that is, when the above formula is an alkyl ester of 5-hydroxy-2-methylhexanoic acid, its specific examples include methyl 5-hydroxy-2-methylhexanoate, ethyl 5-hydroxy-2-methylhexanoate, propyl 5-hydroxy-2-methylhexanoate, butyl 5-hydroxy-2-methylhexanoate, pentyl 5-hydroxy-2-methylhexanoate, hexyl 5-hydroxy-2-methylhexanoate, heptyl 5-hydroxy-2-methylhexanoate, octyl 5-hydroxy-2-methylhexanoate, nonyl 5-hydroxy-2-methylhexanoate, decyl 5-hydroxy-2-methylhexanoate, isopropyl 5-hydroxy-2-methylhexanoate, isobutyl 5-hydroxy-2-methylhexanoate, tert-butyl-5-hydroxy-2-methylhexanoate, 2-methylpentyl 5-hydroxy-2-methylhexanoate and 3-methylpentyl 5-hydroxy-2-methylhexanoate.

(3) $Q_3$=

ester group, $R_2$=$R_3$=methyl group

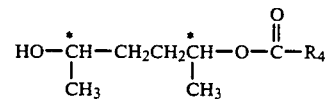

When $R_4$ is a $C_{1-10}$ alkyl group, that is, when the above formula is a 5-acyloxy-2-hexanol, its specific examples include 5-acetyloxy-2-hexanol, 5-propionyloxy-2-hexanol, 5-butyryloxy-2-hexanol, 5-pentanoyloxy-2-hexanol, 5-hexanoyloxy-2-hexanol, 5-heptanoyloxy-2-hexanol, 5-octanoyloxy-2-hexanol, 5-nonanoyloxy-2-hexanol, 5-decyloxy-2-hexanol, 5-isobutyloxy-2-hexanol, 5-isovaleryloxy-2-hexanol and 5-pivaroyloxy-2-hexanol.

B. Optically active dichiral carboxylic acids V (1) $Q_3$=ether group, $R_2$=$R_3$=methyl group

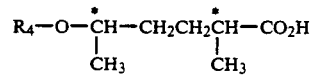

When $R_4$ is a $C_{1-10}$ alkyl group, that is, when the above formula is a 5-alkyloxy-2-methylhexanoic acid, its specific examples include 5-methoxy-2-methylhexanoic acid, 5-ethoxy-2-methylhexanoic acid, 5-propoxy-2-methylhexanoic acid, 5-butoxy-2-methylhexanoic acid, 5-pentyloxy-2-methylhexanoic acid, 5-hexyloxy-2-methylhexanoic acid, 5-heptyloxy-2-methylhexanoic acid, 5-octyloxy-2-methylhexanoic acid, 5-nonyloxy-2-methylhexanoic acid, 5-decyloxy-2-methylhexanoic acid, 5-isopropoxy-2-methylhexanoic acid, 5-isobutoxy-2-methylhexanoic acid, 5-tert-butoxy-2-methylhexanoic acid, 5-(2-methylpentyloxy)-2-methylhexanoic acid and 5-(3-methylpentyloxy)-2-methylhexanoic acid.

(2) $Q_3$=

ester group, $R_2 = R_3 =$ methyl group

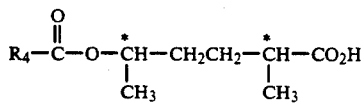

When $R_4$ is a $C_{1-10}$ alkyl group, that is, when the above formula is a 5-acyloxy-2-methylhexanoic acid, its specific examples include 5-acetyloxy-2-methylhexanoic acid, 5-propionyloxy-2-methylhexanoic acid, 5-butyryloxy-2-methylhexanoic acid, 5-pentanoyloxy-2-methylhexanoic acid, 5-hexanoyloxy-2-methylhexanoic acid, 5-heptanoyloxy-2-methylhexanoic acid, 5-octanoyloxy-2-methylhexanoic acid, 5-nonanoyloxy-2-methylhexanoic acid, 5-decyloxy-2-methylhexanoic acid, 5-isobutyryloxy-2-methylhexanoic acid, 5-isovaleryloxy-2-methylhexanoic acid and 5-pivaroyloxy-2-methylhexanoic acid.

Next, there are shown specific examples of the optically active compounds III and V wherein $n = 3-6$.

C. Optically active dichiral secondary alcohols III (1) $Q_3 =$ ether group, $R_2 = R_3 =$ methyl group

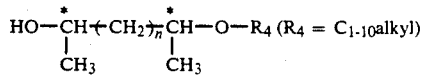

Specific examples include the followings.
n=3 6-Alkyloxy-2-heptanols
n=4 7-Alkyloxy-2-octanols
n=5 8-Alkyloxy-2-nonanols
n=6 9-Alkyloxy-2-decanols (2) $Q_3 =$

ester group, $R_2 = R_3 =$ methyl group

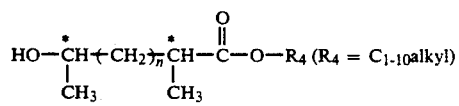

Specific examples include the followings.
n=3 Alkyl 6-hydroxy-2-methylheptanoates
n=4 Alkyl 7-hydroxy-2-methyloctanoates
n=5 Alkyl 8-hydroxy-2-methylnonanoates
n=6 Alkyl 9-hydroxy-2-methyldecanoates (3) $Q_3 =$

ester group, $R_2 = R_3 =$ methyl group

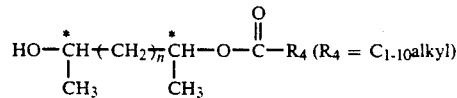

Specific examples include the followings.
n=3 6-Acyloxy-2-heptanols
n=4 7-Acyloxy-2-octanols
n=5 8Acyloxy-2-nonanols
n=6 9-Acyloxy-2-decanols D. Optically active dichiral carboxylic acids V (1) $Q_3 =$ ether group, $R_2 = R_3 =$ methyl group

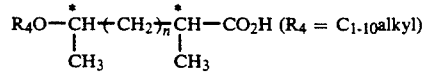

Specific examples include the followings.
n=3 6-Alkyloxy-2-methylheptanoic acids
n=4 7-Alkyloxy-2-methyloctanoic acids
n=5 8-Alkyloxy-2-methylnonanoic acids
n=6 9-Alkyloxy-2-methyldecanoic acids (2) $Q_3 =$

ester group, $R_2 = R_3 =$ methyl group.

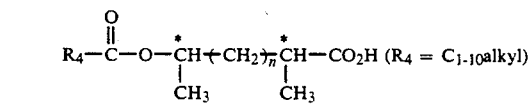

Specific examples include the followings.
n=3 6-Acyloxy-2-methylheptanoic acids
n=4 7-Acyloxy-2-methyloctanoic acids
n=5 8-Acyloxy-2-methylnonanoic acids
n=6 9-Acyloxy-2-methyldecanoic acids Those compounds whose $Q_2$ and $Q_3$ are other than the above-mentioned can also be produced according to the conventional methods.

Next, there are specifically described typical examples of the carboxylic acid II and the alcohol or phenolic hydroxyl group-containing compound IV which are both important materials for formation of the skeletal portion of the optically active compounds of the present invention.

The carboxylic acid II can be classified into two type compounds represented by the following general formulas.

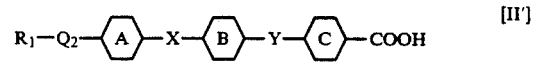

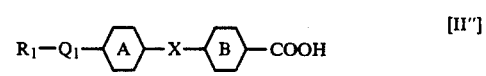

As typical examples of these compounds, there can be mentioned 4-(4'-alkyloxy or alkyl-4-biphenylcarbonyloxy)benzoic acids, 4-(4'-alkyloxy or alkyl-4-biphenyloxycarbonyl)benzoic acids, 4'-(4-alkyloxy or alkylphenylcarbonyloxy)-4-biphenylcarboxylic acids, 4'-(4-alkyloxy or alkylphenyloxycarbonyl)-4-biphenylcarboxylic acids, 4'-(alkyloxy(or alkyl)-4-biphenylcarboxylic acids, 4''-alkyloxy(or alkyl)-4-terphenylcarboxylic acids, 4'-(trans-4-alkyloxy or alkylcyclohexylcarbonyloxy)-4-biphenylcarboxylic acids, trans-4-(4'-alkyloxy or alkyl-4-biphenylcarbonyloxy)cyclohexanecarboxylic acids, 2-[4-(4-alkyloxy or alkylphenylcarbonyloxy)phenyl]pyridimidinyl-5-carboxylic acids, 2-(4'-alkyloxy or alkyl-4-biphenyl)pyrimidinyl-5-carboxylic acids, 4'-(5-alkyloxy or alkylpyrimidinyl-2-oxycarbonyl)biphenyl-4-carboxylic acids, 4'-[2-(5-alkyloxy or alkyl)-2-(pyridyl)ethyl]biphenyl-4-carboxylic acids, 4-[4-(trans-5-alkyloxy or alkyl-1,3-dioxane-2-yl)]-benzoic acids, 4'-[4-(trans-5-alkyloxy or alkyl-1,3-dioxane-2-yl)]biphenyl-4-carboxylic acids, 2-[4-(4-alkyloxy or alkylphenylcarbonyloxy)phenyl]pyrazinyl-5-carboxylic acids, 2-(4'-alkyloxy or alkyl-4-biphenyl)pyrazinyl-5-carboxylic acids, 4'-(5-alkyloxy or alkylpyrazinyl-2-oxycarbonyl)-biphenyl-4-carboxylic acids and 4'-(6-alkyloxy or alkyl-3-pyridazinyl)biphenyl-4-carboxylic acids.

The alcohol IV or the compound IV having a phenolic hydroxy group can be classified into two type compounds represented by the following general formulas.

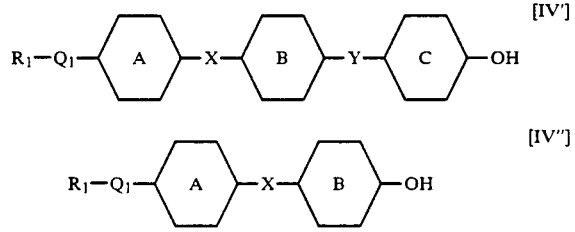

As typical examples of these compounds, there can be mentioned 4-hydroxyphenyl esters of, 4'-alkyloxy or alkylbiphenyl-4-carboxylic acids, 4'-alkyloxy or alkyl-4-biphenyl esters of 4'-hydroxybenzoic acids, 4'-hydroxy-4-biphenyl esters of 4-alkyloxy or alkylbenzoic acids, 4-alkyloxy or alkylphenyl esters of 4'-hydroxybiphenyl-4-carboxylic acids, 4'-hydroxy-4-biphenyl esters of trans-4-alkyloxy or alkylcyclohexanecarboxylic acids, trans-4-hydroxycyclohexyl esters of 4'-alkyloxy or alkyl-4-biphenylcarboxylic acids, 4-(5-hydroxy-2-pyrimidinyl)phenyl esters of 4-alkyloxy or alkylbenzoic acids, 2-(4'-alkyloxy or alkyl-4-biphenyl)pyrimidine-5-ols, 5-alkyloxy or alkyl-2-pyridinyl esters of 4'-hydroxy-4-biphenylcarboxylic acids, 4'-[2-(5-alkyloxy or alkyl-2-pyridyl)ethyl]biphenyl-4-ols, 4-hydroxyphenyl esters of 4-[4-(trans-5-alkyloxy or alkyl)-1,3-dioxane-2-yl]benzoic acids and 5-alkyloxy- or 5-alkyl-2-pyrazinyl esters of 4'-hydroxy-4-biphenylcarboxylic acids.

As specific examples of the thiol or thiophenolic compound IV, there can be mentioned thiol or thiophenolic compounds corresponding to the above-mentioned alcohol or phenolic hydroxyl group-containing compounds.

In the above there have been mentioned typical examples of the optically active dichiral alcohol and the optically active dichiral carboxylic acid which are both important materials for formation of the optically active dichiral side chain portion of the optically active compound of the present invention, as well as typical examples of the (thio)alcohol or (thio)phenolic hydroxyl group-containing compound which are both important materials for formation of the skeletal portion of the optically active compound of the present invention. Specific examples for preparation of the optically active compound of the present invention are described later; however, the preparation of the present compound is not restricted thereto, and the present compound can be prepared by appropriately selecting one of the above-mentioned materials for formation of the skeletal portion and one of the above-mentioned materials for formation of the optically active dichiral portion. The optically active compound of the present invention includes the following specific examples.

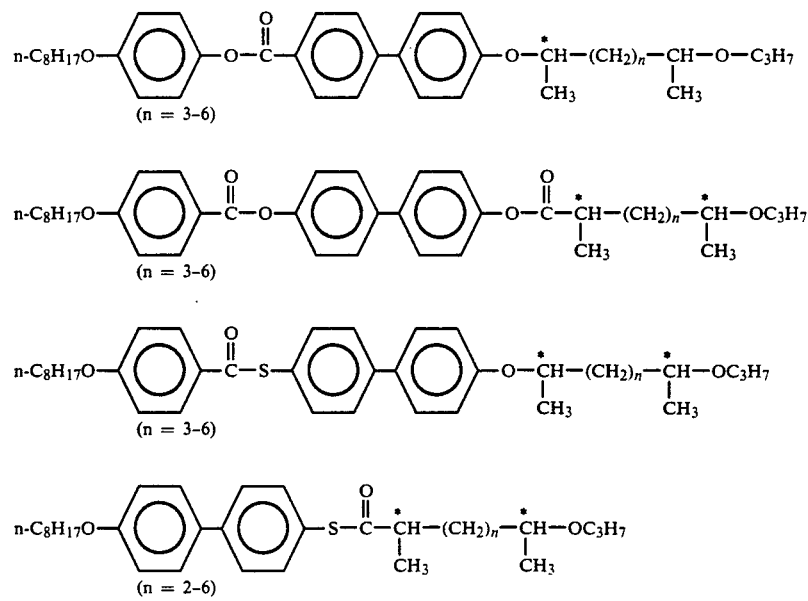

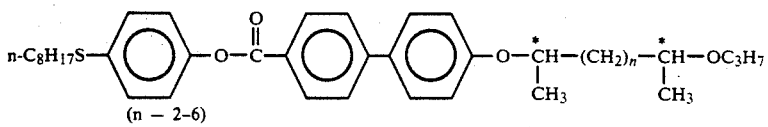

-continued

The optically active compounds I of the present invention have a structure in which each asymmetric carbon atom bonds to oxygen, sulfur or (thio)carbonyl, and therefore the compounds generally show high spontaneous polarization. In addition, most of the compounds I show a chiral smectic C (Sc*) phase which is a liquid crystal phase suitable for display methods utilizing the ferroelectric properties of liquid crystals, and the temperature range of the chiral smectic C phase is low and wide.

The optically active compounds of the present invention are very stable to heat, light, water and air. Accordingly, in putting the compounds to practical use as or in liquid crystal materials, there can be eliminated inconveniences such as arrangements of an apparatus for prevention of overheating, a glass frit seal for prevention of moisture absorption or permeation, etc.

The optically active compounds I of the present invention may be used alone. However, having excellent compatibility with conventionally known liquid crystal compounds such as those of Schiff's base type, biphenyl type, phenylcyclohexane type, heterocyclic type and the like, the compounds can be made into liquid crystal compositions having excellent properties, by incorporating them into said liquid crystal compounds.

As the liquid crystal compounds into which the optically active compounds I of the present invention can be incorporated, there can be mentioned, for example, ferroelectric liquid crystal compounds as well as liquid crystal compounds showing a smectic C phase. The ferroelectric liquid crystal compounds include, for example, biphenyl type liquid crystals described in JP-A-118744/1984 and 13729/1985, ester type liquid crystals described in JP-A-128357/1984, 51147/1985, 2051/1986 and 249953/1986, and pyrimidine type liquid crystals described in JP-A-260564/1985, 24756/1986, 5368/1986 and 215373/1986. The liquid crystal compounds showing a smectic C phase include, for example, ester type liquid crystal compounds described in JP-A-228036/1987, and cyclohexane type liquid crystals and heterocyclic type liquid crystals described in the materials of the 16th Freiburg Liquid Crystal Forum (Mar. 21, 1986) and the materials of the First International Symposium on Ferroelectric Liquid Crystals (Sep. 21, 1987).

The liquid crystal compositions of the present invention can be prepared by mixing the optically active compounds of the present invention with the nematic or cholesteric liquid crystals described in "Flüssige Kristalle in Tabellen" I & II, VEB-Verlag, Leipzig, or by mixing with commercially available nematic liquid crystal compounds. When the optically active compounds of the present invention are mixed with nematic liquid crystals, the twisting direction of the cholesteric pitch and the pitch length of the resulting nematic liquid crystal compositions can be freely controlled via the amount of the present compound added.

When the optically active compound of the present invention is mixed with other liquid crystals as mentioned above, the mixing ratio can be selected depending upon the application purpose of the resulting liquid crystal composition. For example, when it is desired to prepare a ferroelectric liquid crystal composition, the optically active compound of the present invention can be used in an amount of 5–50% by weight based on the total weight of the composition; when a nematic liquid crystal composition is prepared, the compound of the present invention can be used in an amount of 0.1–5% by weight.

As liquid crystal optical modulators, there can be mentioned various display apparatuses using a plurality of liquid crystal devices, for example, display apparatuses used in word processor, lap top type personal computer, work station, etc., image display apparatuses used in TV set, video telephone, etc. and terminal display panels of optical communication apparatuses.

Various types of liquid crystal display devices are known. The liquid crystal compositions of the present invention can be used in any liquid crystal display device as long as the compositions can exhibit the capabilities effectively. The liquid crystal compositions of the present invention can be effectively used in, for example, the liquid crystal devices disclosed in U.S. Pat. No. 4,367,924, JP-B-63-22287, U.S. Pat. No. 4,563,059, etc.

Generally, these liquid crystal devices are basically constituted by a pair of substrates, two polarizing plates provided on the substrates, a pair of transparent electrodes, a pair of molecule alignment layers, a liquid crystal composition sealed between the substrates by a sealing agent, and a reflecting plate.

The present invention is described more specifically by way of Examples and Application Example.

The optically active compounds prepared in Examples were measured for phase, phase transition temperature and spontaneous polarization. The results are listed in Table 1.

Incidentally, phase and phase transition temperature were measured using a polarizing microscope and a differential scanning calorimeter (DSC).

Spontaneous polarization was measured by the Sowyer-Tower method. The values of spontaneous polarization are those at a temperature lower by 10° C. than the upper limit temperature of chiral smectic C phase.

The phases such as liquid crystal phase are shown by the following abbreviations.
Iso: isotropic phase
N*: chiral nematic phase
$S_A$: smectic A phase
K: crystalline phase
Sc*: chiral smectic C phase
$S_1$ and $S_2$ smectic phase which are difficult to identify

REFERENCE EXAMPLE 1

Preparation of (2S, 5S)-5-alkoxy-2-hexanols 2,5-Hexanedione was subjected to reduction by a baker's yeast in accordance with the method described in a literature [J. K. Lieser, Syn. Commun., 13, 765 (1983)] to obtain (2S,5S)-2,5-hexanediol. The product was reacted with an equivalent mole of a corresponding alkyl iodide in N-dimethylformamide in the presence of 60% oily sodium hydride containing an equivalent mole of the active component, to obtain the title compounds as an oily substance, respectively.

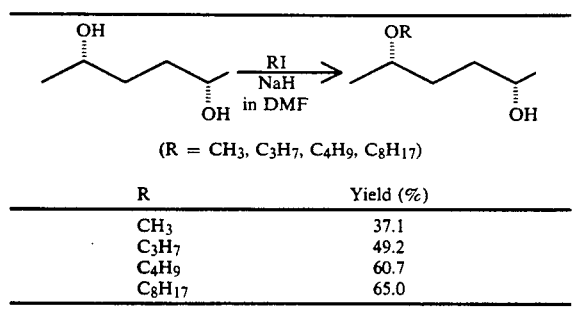

(R = CH₃, C₃H₇, C₄H₉, C₈H₁₇)

| R | Yield (%) |
|---|---|
| CH₃ | 37.1 |
| C₃H₇ | 49.2 |
| C₄H₉ | 60.7 |
| C₈H₁₇ | 65.0 |

As an example of the physical constants of the title compounds obtained above, there are shown below the $^1$H-NMR spectral data of (2S,5S)-5-methoxy-2-hexanol.

$^1$H-NMR (90 MHz, CDCl₃) δ: 1.15(3H, d, j=6.3H), 1.18(3d, d, j=6.3 Hz), 1.54(4H, t, j=2.8 Hz), 2.46(1H, broad s), 3.32(3H, s), 3.35(1H, m), 3.75(1H, m)

REFERENCE EXAMPLE 2

Preparation of (2R,5S)-5-butoxy-2-hexanol

The (2S,5S)-5-butoxy-2-hexanol obtained in Reference Example 1 was subjected to inversion at the 2-position hydroxyl group according to the method described in a literature [O. Mitsunobu and E. Eguchi, Bull, Chem. Soc. Japan. 44, 3427 (1971)] to obtain the title compound.

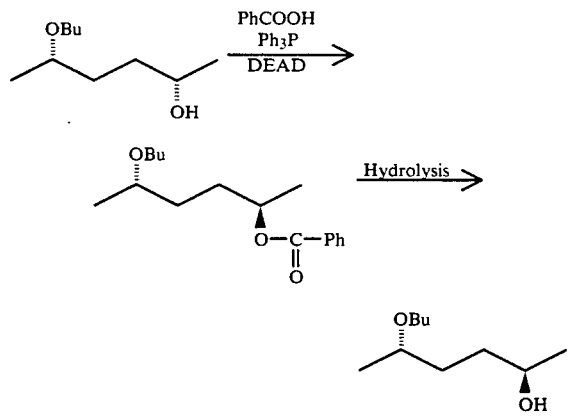

That is, 1.23 g of (2S,5S)-5-butoxy-2-hexanol, 0.86 g of benzoic acid and 2.78 g of triphenylphosphine were dissolved in 25 ml of dry ether. Thereto was dropwise added 2.29 g of diethyl azodicarboxylate (DEAD) at room temperature with stirring. The mixture was stirred for 1 hour at room temperature. The reaction mixture was concentrated under reduced pressure. The residue was separated and purified by silica gel column chromatography (eluting solvent: dichloromethane) to obtain 1.56 g of (2R,5S)-5-butoxy-2-hexyl benzoate as a colorless oily substance. 1.56 g of the product was dissolved in 20 ml of methanol. Thereto was dropwise added 516 ml of a 1 N methanol solution of sodium hydroxide at room temperature with stirring. The mixture was stirred for 8 hours at room temperature. The reaction mixture was mixed with 15 ml of water and stirred for 8 hours. To the resulting reaction mixture was added water. Then, extraction with dichloromethane was effected. The extract was dried and concentrated. The residue was subjected to Kugel-rohr distillation under reduced pressure to obtain 0.57 g of the title compound as a colorless oil.

$^1$H-NMR (90 MHz; CDCl₃) δ: 0.92(3H, t, j=6.5 Hz), 1.14(3H, d, j=6.0 Hz), 1.18(3H, d, j=6.0 Hz), 1.40~1.70(10H, m), 2.41(1H, broad s), 3.21~3.59 (3H, , m), 3.62~3.93(1H, m).

REFERENCE EXAMPLE 3

(2R,5S)-2-methyl-5-propoxyhexanoic acid

The title compound was synthesized using, as a starting material, the (2R,5S)-5-propoxy-2-hexanol obtained in Reference Example 1, according to the following scheme.

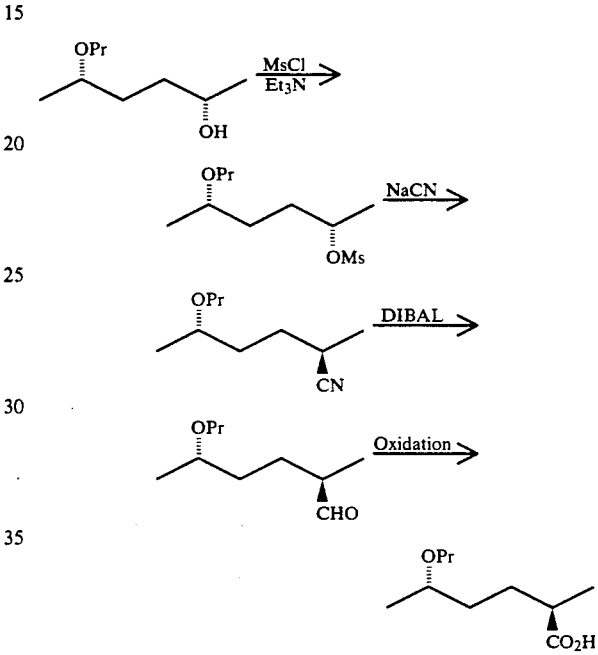

That is, in 10 ml of dichloromethane were dissolved 1.45 g of (2S,5S)-5-propoxy-2-hexanol and 1.09 g of methanesulfonyl chloride. Thereto was dropwise added 0.96 g of triethylamine with stirring under ice cooling. The mixture was stirred for 4 hours under ice cooling. The reaction mixture was poured into water. The organic layer was separated, washed with diluted hydrochloric acid and an aqueous sodium hydrogencarbonate solution in this order, dried and concentrated to obtain 1.98 g of a crude mesyl compound as an oil. The product was dissolved in 25 ml of dimethyl sulfoxide (DMSO). Thereto was added 1.7 g of sodium cyanide. The mixture was stirred for 2 hours at 60° C. The reaction mixture was poured into water. Extraction with dichloromethane was effected. The extract was dried and concentrated. The residue was separated and purified by silica gel column chromatography (eluting solvent: n-hexane-ethyl acetate (9:1)] to obtain, as a colorless oily substance, 1.8 g (2R,5S)-2-methyl-5-propoxypentranenitrile. 1.8 g of this product was dissolved in 30 ml of dry toluene. Thereto was dropwise added 14 ml of a toluene solution containing 1.5 mole % of diisobutylaluminum hydride (DIBAL), with stirring at −78° C. The mixture was stirred for 30 minutes at −78° C. To the reaction mixture was dropwise added 1 ml of concentrated hydrochloric acid with stirring. Then, diluted hydrochloric acid was added. The organic layer was separated and concentrated under reduced pressure to obtain an aldehyde compound as an oil. The product was dissolved in 50 ml of acetone. Thereto was dropwise added a Jones' reagent with stirring under ice cooling. The reaction mixture was poured into water. Extraction with dichloromethane was effected. The extract was dried and concentrated. The residue was subjected to Kugel-rohr distillation under reduced pressure to obtain 0.88 g of the title compound as a colorless oil.

$^1$H-NMR (90 MHz, CDCl$_3$) δ: 0.92(3H, t, j=7.6 Hz), 1.13(3H, d, j=6.0 Hz), 1.19(3H, d, j=6.8 Hz), 1.32~1.39(6H, m), 2.20~2.63(1H, m), 3.14~3.59(3H, m).

IR $v_{max}^{neat}$ cm$^{-1}$: 1710, 1470, 1090.

EXAMPLE 1

4-Octyloxyphenyl ester of 4'-[1R,4S)-1-methyl-4-methoxypentyloxy]-4-biphenyl-carboxylic acid In 30 ml of dry tetrahydrofuran were dissolved 0.26 g of the (2S,5S)-5-methoxy-2-hexanol obtained in Reference Example 1, 0.8 g of 4-octyloxyphenyl 4'-hydroxy-4-biphenylcarboxylate and 0.9 g of triphenylphosphine. Thereto was dropwise added 0.61 g of diethyl azodicarboxylate. The mixture was stirred for about 1 hour at room temperature and then concentrated under reduced pressure. The residue was separated and purified by silica gel column chromatography (developing solvent: carbon tetrachloride-ethyl acetate (20:1)], followed by recrystallization from methanol to obtain 0.14 g of the title compound.

The elemental analysis of the compound is shown below.

Elemental analysis: Calcd. for C$_{33}$H$_{42}$O$_5$: C, 76.66; H, 8.33. Found: C, 76.54; H, 8.31.

EXAMPLE 2

4-Octyloxyphenyl ester of 4'-[(1R,4S)-1-methyl-4-propoxypentyloxy]-4-biphenyl-carboxylic acid Using 0.34 g of the (2S,5S)-5-propoxy-2-hexanol and 0.8 g of 4-octyloxyphenyl 4'-hydroxy-4-biphenylcarboxylate, there was obtained 0.534 g of the title compound in the same manner as in Example 1.

The elemental analysis of the compound is shown below.

Elemental analysis: Calcd. for C$_{36}$H$_{48}$O$_5$: C, 77.11; H, 8.63. Found: C, 77.21; H, 8.64.

EXAMPLE 3

4-Octyloxyphenyl ester of 4'-[(1R,4S)-1-methyl-4-butoxypentyloxy]-4-biphenyl-carboxylic acid Using 0.37 g of the (2S,5S)-5-butoxy-2-hexanol obtained in Reference Example 1 and 0.8 g of 4-octyloxyphenyl 4'-hydroxy-4-biphenylcarboxylate, there was obtained 0.394 g of the title compound in the same manner as in Example 1.

The elemental analysis of the compound is shown below.

Elemental analysis: Calcd. for C$_{37}$H$_{50}$O$_5$: C, 77.31; H, 8.77. Found: C, 77.41; H, 8.81.

EXAMPLE 4

4-Octyloxyphenyl ester of 4'-[(1R,4S)-1-methyl-4-octyloxypentyloxy]-4-biphenyl-carboxylic acid Using 0.48 g of the (2S,5S)-5-octyloxy-2-hexanol obtained in Reference Example 1 and 0.8 g of 4-octyloxyphenyl 4'-hydroxy-4-biphenylcarboxylate, there was obtained 0.141 g of the title compound in the same manner as in Example 1.

The elemental analysis of the compound is shown below.

Elemental analysis: Calcd. for C$_{41}$H$_{59}$O$_5$: C, 77.93; H, 9.41. Found: C, 78.18; H, 9.33.

EXAMPLE 5

4'-Octyloxy-4-biphenylyl ester of 4-[(1R,4S)-1-methyl-4-methoxy-pentyloxy]-benzoic acid Using 0.28 g of the (2S,5S)-5-methoxy-2-hexanol obtained in Reference Example 1 and 0.8 g of 4'-octyloxy-4-biphenylyl 4-hydroxybenzoate, there was obtained 0.70 g of the title compound in the same manner as in Example 1.

The elemental analysis of the compound is shown below.

Elemental analysis: Calcd. for C$_{34}$H$_{44}$O$_5$: C, 76.66; H, 8.33. Found: C, 76.50; H, 8.33.

EXAMPLE 6

4'-[(1R,4S)-1-methyl-4-propoxypentyloxy]-4-biphenylyl ester of 4-octyloxybenzoic acid Using 0.34 g of the (2S,5S)-5-propoxy-2-hexanol obtained in Reference Example 1 and 0.8 g of 4'-hydroxy-4-biphenylyl 4-octyloxybenzoate, there was obtained 0.48 g of the title compound in the same manner as in Example 1.

The elemental analysis of the compound is shown below.

Elemental analysis: Calcd. for C$_{36}$H$_{48}$O$_5$: C, 77.11; H, 8.63. Found: C, 77.17; H, 8.74.

EXAMPLE 7

4-[(1R,4S)-1-Methyl-4-propoxypentyloxy]-4'-octyloxybiphenyl

Using 0.47 g of the (2S,5S)-5-propoxy-2-hexanol obtained in Reference Example 1 and 0.8 g of 4-hydroxy-4'-octyloxybiphenyl, there was obtained 0.311 g of the title compound in the same manner as in Example 1.

The elemental analysis of the compound is shown below.

Elemental analysis: Calcd. for C$_{29}$H$_{44}$O$_3$: C, 79.04; H, 10.06. Found: C, 79.16; H, 10.08.

EXAMPLE 8

4-Octyloxyphenyl ester of 4'-[(1S,4S)-1-methyl-4-butoxypentyloxy]-4-biphenyl-carboxylic acid Using 0.37 g of the (2R,5S)-5-butoxy-2-hexanol obtained in Reference Example 2 and 0.8 g of 4-octylphenyl 4'-hydroxy-4-biphenylcarboxylic acid, there was obtained 0.495 g of the title compound in the same manner as in Example 1.

The elemental analysis of the compound is shown below.

Elemental analysis: Calcd. for $C_{37}H_{50}O_5$: C, 77.31; H, 8.77. Found: C, 77.37; H, 8.88.

EXAMPLE 9

4'-Octyloxy-4-biphenylyl (2R,5S)-2-methyl-5-butoxyhexanoate

The (2R,5S)-2-methyl-5-propoxyhexanolic acid obtained in Reference Example 3 was reacted with oxalyl chloride to obtain (2R,5S)-2-methyl-5-propoxyhexanoic acid chloride. 0.35 g of the product and 0.5 g of 4-hydroxy-4'-octyloxy-biphenyl were reacted in THF in the presence of triethylamine. The reaction mixture was subjected to the same procedure as in Example 1 to obtain 0.205 g of the title compound.

The elemental analysis of the compound is shown below.

Elemental analysis: Calcd. for $C_{30}H_{44}O_5$: C, 76.88; H, 9.46. Found: C, 76.59; H, 9.53.

EXAMPLE 10

3-[(1S,4S)-1-methyl-4-propoxypentyloxy]-6-(4-octyloxyphenyl)pyridazine 320 mg (2.0 mM) of the (2S,5S)-5-propoxy-2-hexanol obtained in Reference Example 1 was dissolved in 15 ml of anhydrous toluene. Thereto was added metallic sodium with stirring at room temperature. To the mixture was added 478 g (1.5 mM) of 3-chloro-6-(4-octyloxyphenyl)pyridazine. The resulting mixture was refluxed for 3 hours. The reaction mixture was cooled and mixed with water and toluene. The toluene layer was separated and concentrated under reduced pressure. The residue was subjected to silica gel column chromatography [eluting solvent: n-hexane-ethyl acetate (4:1)] to obtain 190 mg of the title compound.

The elemental analysis of the compound is shown below.

Elemental analysis: Calcd. for $C_{27}H_{42}N_2O_3$: C, 73.26; H, 9.56. Found: C, 73.29; H, 9.61.

TABLE 1

| Example | Chemical structure | Phase transition temperature (°C.) | Spontaneous polarization (nC/cm²) |
|---|---|---|---|
| 1 | n-C$_8$H$_{17}$O–⌬–COO–⌬–⌬–O–(R)CH(CH$_3$)–CH$_2$–CH$_2$–(S)CH(CH$_3$)–OCH$_3$ | K $\underset{28.9}{\overset{62.7}{\rightleftarrows}}$ S$_1$ $\underset{35.6}{\rightleftarrows}$ Sc* $\underset{72.3}{\rightleftarrows}$ Ch $\underset{106.5}{\rightleftarrows}$ Iso | 67.5 |
| 2 | n-C$_8$H$_{17}$O–⌬–COO–⌬–⌬–O–(R)CH(CH$_3$)–CH$_2$–CH$_2$–(S)CH(CH$_3$)–OPr | K $\underset{59.0}{\overset{76.5}{\rightleftarrows}}$ Sc* $\underset{78.3}{\rightleftarrows}$ N* $\underset{110.5}{\rightleftarrows}$ Iso | 32 (73° C.) |
| 3 | n-C$_8$H$_{17}$O–⌬–COO–⌬–⌬–O–(R)CH(CH$_3$)–CH$_2$–CH$_2$–(S)CH(CH$_3$)–OBu | K $\underset{20.3}{\overset{61.0}{\rightleftarrows}}$ Sc* $\underset{75.6}{\rightleftarrows}$ N* $\underset{88.9}{\rightleftarrows}$ Iso | 95 |
| 4 | n-C$_8$H$_{17}$O–⌬–COO–⌬–⌬–O–(R)CH(CH$_3$)–CH$_2$–CH$_2$–(S)CH(CH$_3$)–OC$_8$H$_{17}$(n) | K $\underset{24.8}{\overset{50.1}{\rightleftarrows}}$ Sc* $\underset{71.1}{\rightleftarrows}$ N* $\underset{84.2}{\rightleftarrows}$ Iso | 57.5 |
| 5 | n-C$_8$H$_{17}$O–⌬–COO–⌬–⌬–O–(R)CH(CH$_3$)–CH$_2$–CH$_2$–(S)CH(CH$_3$)–OPr | K $\underset{18.8}{\overset{67.0}{\rightleftarrows}}$ Sc* $\underset{77.1}{\rightleftarrows}$ N* $\underset{93.4}{\rightleftarrows}$ Iso | 99.0 |
| 6 | n-C$_8$H$_{17}$O–⌬–COO–⌬–⌬–O–(R)CH(CH$_3$)–CH$_2$–CH$_2$–(S)CH(CH$_3$)–OPr | K $\underset{}{\overset{75.5}{\rightleftarrows}}$ S$_1$ $\underset{62.5}{\rightleftarrows}$ Sc* $\underset{81.0}{\rightleftarrows}$ N* $\underset{101.0}{\rightleftarrows}$ Iso | 32.5 |
| 7 | n-C$_8$H$_{17}$O–⌬–⌬–O–(S)CH(CH$_3$)–CH$_2$–CH$_2$–(S)CH(CH$_3$)–OPr | K $\underset{28.4}{\overset{37.4}{\rightleftarrows}}$ Iso | |
| 8 | n-C$_8$H$_{17}$O–⌬–COO–⌬–⌬–O–(S)CH(CH$_3$)–CH$_2$–CH$_2$–(S)CH(CH$_3$)–OBu | K $\underset{22.2}{\overset{57.2}{\rightleftarrows}}$ Sc* $\underset{73.4}{\rightleftarrows}$ N* $\underset{85.6}{\rightleftarrows}$ Iso | 52.5 |

TABLE 1-continued

| Example | Chemical structure | Phase transition temperature (°C.) | Spontaneous polarization (nC/cm²) |
|---|---|---|---|
| 9 | n-C₈H₁₇O—⟨phenyl⟩—⟨phenyl⟩—O—C(=O)—(R)*CH—CH₂—CH₂—(S)*CH(CH₃)—OPr, CH₃ | K ⇌ (27.4/29.2) Iso | |
| 10 | n-C₈H₁₇O—⟨phenyl⟩—N=N—⟨phenyl⟩—O—(S)*CH(CH₃)—CH₂—CH₂—(S)*CH(CH₃)—OPr | K ⇌ (68.0/75.3) Iso | |
| 11 | n-C₈H₁₇O—⟨phenyl⟩—C(=O)O—⟨phenyl⟩—O—(R)*CHCH₂CH₂(S)*CH(CH₃)—OPr, CH₃ | K ⇌ (−6.4/13.8) Sc* ⇌ (−3.9) S_A ⇌ (−2.0/21.0) Iso | |
| 12 | n-C₈H₁₇O—⟨pyridyl⟩—⟨phenyl⟩—O—(R)*CH(CH₃)—CH₂CH₂—(S)*CH(CH₃)—OPr | K ⇌ (−52.8/−55.2) Iso | |
| 13 | n-C₈H₁₇O—⟨phenyl⟩—⟨pyridyl⟩—⟨phenyl⟩—O—(R)*CHCH₂CH₂(S)*CH(CH₃)—OPr, CH₃ | K ⇌ (−7.4/20.4) Sc* ⇌ (37.0) N* ⇌ (42.9) Iso | 38.0 |
| 14 | n-C₈H₁₇O—⟨phenyl⟩—⟨phenyl⟩—C(=O)S—⟨phenyl⟩—O—(R)*CHCH₂CH₂(S)*CH(CH₃)—OPr, CH₃ | K ⇌ S₂ (44.4) S₁ (92.8) Sc* (143.2) S_A (152.7) Iso | 43.0 |
| 15 | n-C₈H₁₇O—⟨phenyl⟩—C(=O)O—⟨phenyl⟩—O—(R)*CHCH₂CH₂(S)*CH(CH₃)—OPr, CH₃ | K ⇌ (11.3/35.0) Sc* ⇌ (35.4) N* ⇌ (54.5) Iso | 62.5 |
| 16 | n-C₈H₁₇O—⟨phenyl⟩—⟨phenyl⟩—O—C(=O)—(R)*CHCH₂CH₂(S)*CH(CH₃)—OPr, CH₃ | K ⇌ (13.1/29.2) Iso | |

TABLE 1-continued

| Example | Chemical structure | Phase transition temperature (°C) | Spontaneous polarization (nC/cm²) |
|---|---|---|---|
| 17 | n-C₈H₁₇S—[pyridine]—[phenyl]—O—CH(CH₃)CH₂CH(CH₃)—OPr  (R)*, (S)* | Oil | |
| 18 | H₂C=CH—(CH₂)₆—O—[phenyl]—[phenyl]—O—CH(CH₃)CH₂CH(CH₃)—OPr  (R)*, (S)* | K $\xrightleftharpoons[13.6]{1.9}$ Iso | |
| 19 | n-C₈H₁₇O—[phenyl]—C(=O)O—[phenyl]—[phenyl]—O—C(=O)—CH(CH₃)CH₂CH(CH₃)—OPr  (S)*, (S)* | K $\xrightleftharpoons[43.5]{26.9}$ Sc* $\xrightleftharpoons[102.6]{}$ N* $\xrightleftharpoons[111.1]{}$ Iso | 31.0 |
| 20 | n-C₈H₁₇O—[phenyl]—[phenyl]—O—C(=O)—CH(CH₃)CH₂CH(CH₃)—OPr  (S)*, (S)* | K $\xrightleftharpoons[25.4]{22.6}$ Iso | |

EXAMPLES 11-18

The elemental analysis of the compounds is as follows.

TABLE 1A

| Example | Chemical structure | Formula | Analysis (%) Calcd. | Analysis (%) Found |
|---|---|---|---|---|
| 11 | n-C$_8$H$_{17}$O–⟨⟩–C(=O)–O–⟨⟩–O–*CH(CH$_3$)CH$_2$CH$_2$*CH(CH$_3$)–OPr  (R),(S) | C$_{30}$H$_{44}$O$_5$ (484.68) | C: 74.34  H: 9.15 | C: 74.21  H: 9.27 |
| 12 | n-C$_8$H$_{17}$–⟨N,N⟩–⟨⟩–O–*CH(CH$_3$)–CH$_2$CH$_2$–*CH(CH$_3$)–OPr  (R),(S) | C$_{27}$H$_{42}$N$_2$O$_2$ (426.64) | C: 76.01  H: 9.92  N: 6.57 | C: 75.71  H: 10.05  N: 6.53 |
| 13 | n-C$_8$H$_{17}$–⟨⟩–⟨N,N⟩–⟨⟩–O–*CH(CH$_3$)CH$_2$CH$_2$*CH(CH$_3$)–OPr  (R),(S) | C$_{33}$H$_{46}$N$_2$O$_2$ (502.74) | C: 78.84  H: 9.22  N: 5.57 | C: 78.68  H: 9.38  N: 5.42 |
| 14 | n-C$_8$H$_{17}$O–⟨⟩–⟨⟩–C(=O)–S–⟨⟩–O–*CH(CH$_3$)CH$_2$CH$_2$*CH(CH$_3$)–OPr  (R),(S) | C$_{36}$H$_{48}$O$_4$S (576.84) | C: 74.96  H: 8.39 | C: 75.06  H: 8.46 |
| 15 | n-C$_8$H$_{17}$–⟨⟩–O–C(=O)–⟨⟩–⟨⟩–O–*CH(CH$_3$)CH$_2$CH$_2$*CH(CH$_3$)–OPr  (R),(S) | C$_{36}$H$_{48}$O$_4$ (544.78) | C: 79.37  H: 8.88 | C: 79.51  H: 9.01 |
| 16 | n-C$_8$H$_{17}$O–⟨⟩–⟨⟩–C(=O)–O–*CH(CH$_3$)CH$_2$CH$_2$*CH(CH$_3$)–OPr  (R),(S) | C$_{30}$H$_{44}$O$_4$ (468.68) | C: 76.88  H: 9.46 | C: 76.65  H: 9.60 |
| 17 | n-C$_8$H$_{17}$S–⟨N,N⟩–⟨⟩–O–*CH(CH$_3$)CH$_2$CH$_2$*CH(CH$_3$)–OPr  (R),(S) | C$_{27}$H$_{42}$N$_2$O$_2$S (458.71) | C: 70.70  H: 9.23  N: 6.11 | C: 70.50  H: 9.44  N: 5.96 |
| 18 | H$_2$C=CH–(CH$_2$)$_6$–O–⟨⟩–⟨⟩–O–*CH(CH$_3$)CH$_2$CH$_2$*CH(CH$_3$)–OPr  (R),(S) | C$_{29}$H$_{42}$O$_3$ (438.65) | C: 79.41  H: 9.65 | C: 79.40  H: 9.85 |
| 19 | n-C$_8$H$_{17}$O–⟨⟩–O–C(=O)–⟨⟩–⟨⟩–O–C(=O)–*CH(CH$_3$)CH$_2$CH$_2$*CH(CH$_3$)–OPr  (S),(S) | C$_{37}$H$_{48}$O$_6$ (588.78) | C: 75.48  H: 8.22 | C: 75.61  H: 8.34 |
| 20 | n-C$_8$H$_{17}$O–⟨⟩–⟨⟩–O–C(=O)–*CH(CH$_3$)–CH$_2$CH$_2$*CH(CH$_3$)–OPr  (S),(S) | C$_{30}$H$_{44}$O$_4$ (468.68) | C: 76.88  H: 9.46 | C: 76.80  H: 9.26 |

These compounds were obtained in the similar manner as in Example 1 from the corresponding core-compounds (containing the non-chiral side chains) and the chiral compounds.

EXAMPLE 19

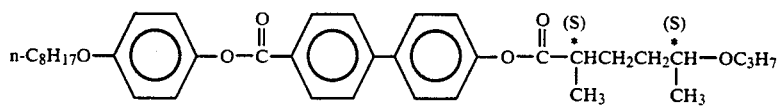

(i) (2S,5S)-2-Methyl-5-propoxyhexanoic acid

The title compound was prepared by a known path way from a starting material, the (2S,5S)-5-propoxy-2-hexanol obtained in Reference Example 1 according to the following scheme.

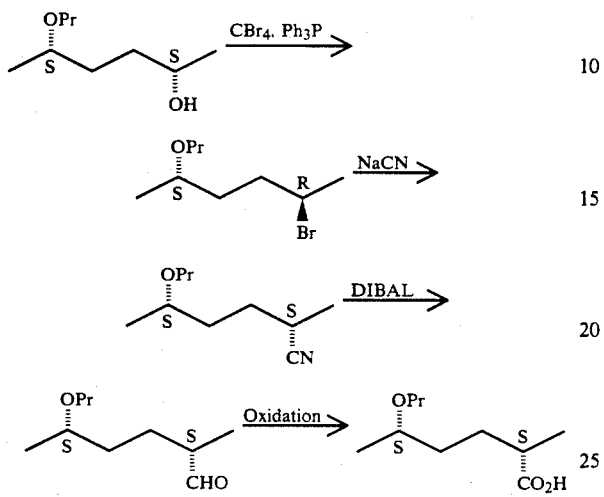

(ii) Esterification

The (2S,5S)-2-methyl-5-propoxyhexanoic acid prepared above was reacted with oxalyl chloride to obtain (2R,5S)-2-methyl-5-propoxyhexanoic acid chloride. The title compound was prepared in the same manner as in Example 9 from the acid chloride obtained above and the corresponding core-compound, 4-octyloxyphenyl 4'-hydroxy-4-biphenylcarboxylate.

EXAMPLE 20

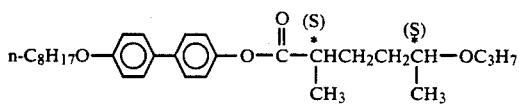

The (2S,5S)-2-methyl-5-propoxyhexanoic acid obtained in Example 19 was subjected to the reaction with oxalyl chloride to give the corresponding acid chloride. The title compound was prepared in the same manner as in Example 9 from the acid chloride obtained above and the corresponding core-compound, 4'-octyloxy-4-biphenol.

The elemental analysis of the compounds obtained in Examples 19 and 20 are also shown in Table 1A.

APPLICATION EXAMPLE

The optically active compounds of the present invention shown in Examples were incorporated into the known ferroelectric liquid crystal compounds A to C (hereinafter referred to as mother liquid crystals) shown in Table 2, in given amounts, to prepare liquid crystal compositions shown in Table 3 each containing an optically active compound of the present invention.

These compositions and the mother liquid crystals A-C were measured for spontaneous polarization. The results are shown in Table 3.

In Table 3, the values of spontaneous polarization are those at a temperature lower by 10° C. than the upper limit temperature of chiral smectic C phase.

TABLE 2

| Mother liquid crystal | Chemical structure |
|---|---|
| A | $C_8H_{17}O$—⟨⟩—CH=N—⟨⟩—$CO_2CH_2\overset{*}{C}HC_2H_5$ $\vert$ $CH_3$ |
| | $C_8H_{17}O$—⟨⟩—⟨⟩—$CO_2CH_2\overset{*}{C}HC_2H_5$ $\vert$ $CH_3$ (equimolar mixture) |
| B | $C_7H_{15}O$—⟨⟩—$CO_2$—⟨⟩—$O(CH_2)_3\overset{*}{C}HC_2H_5$ $\vert$ $CH_3$ |
| C | $C_7H_{15}O$—⟨⟩—OCO—⟨⟩—$O(CH_2)_3\overset{*}{C}HC_2H_5$ $\vert$ $CH_3$ |
| | $C_7H_{15}O$—⟨⟩—OCO—⟨⟩—$O(CH_2)_5\overset{*}{C}HC_2H_5$ $\vert$ $CH_3$ (equimolar mixture) |

TABLE 3

| Mother liquid crystal | Optically active compound of present invention | | Spontaneous polarization ($nC/cm^2$) |
|---|---|---|---|
| | Example No. | Amount used (wt. %) | |
| A | — | — | 4 |
| A | 1 | 10 | 8 |
| A | 3 | 10 | 11 |
| A | 8 | 20 | 12 |
| B | — | — | <1 |
| B | 1 | 20 | 12 |
| B | 2 | 10 | 5 |
| B | 3 | 10 | 10 |
| B | 6 | 10 | 5 |
| B | 9 | 20 | 20 |
| C | — | — | <1 |
| C | 1 | 30 | 18 |
| C | 6 | 10 | 10 |
| C | 7 | 20 | 15 |

Each liquid crystal composition shown in Table 3 was sealed in a cell constituted by (a) two glass substrates each with a transparent electrode, obtained by spin coating of a polyimide and subsequent rubbing and (b) a spacer consisting of a polyethylene terephthalate film of 6 μm in thickness, whereby liquid crystal devices were prepared. A rectangular wave (40 Vp-p) was applied to the liquid crystal devices at room temperature, and their optical responses were observed by a polarizing microscope. The devices containing the compositions using the optically active compounds of the present invention gave an optical contrast and showed a very good optical response, while the devices containing the mother liquid crystal B or C alone showed no clear optical response.

As is clear from Examples and Application Example, the present invention provides liquid crystal compounds and liquid crystal compositions having a large spontaneous polarization and showing a chiral smectic C phase. Accordingly, the optically active compounds of the present invention and the liquid crystal compositions containing these compounds are useful as a liquid crystal to be employed in optical modulators such as liquid crystal display apparatuses and can provide such apparatuses having excellent capabilities in response etc.

What is claimed is:

1. An optically active compound represented by the formula:

$$R_1-Q_1-M-Q_2-\overset{*}{C}H-(CH_2)_2-\overset{*}{C}H-Q_3-R_4$$
$$\phantom{R_1-Q_1-M-Q_2-}|\phantom{-(CH_2)_2-}|$$
$$\phantom{R_1-Q_1-M-Q_2-}R_2\phantom{-(CH_2)_2-}R_3$$

wherein
   $R_1$ is a straight chain alkyl group of 6 to 12 carbon atoms or a straight chain alkenyl group of 6 to 12 carbon atoms;
   $R_2$ and $R_3$ are independently a lower alkyl group of 1 to 3 carbon atoms;
   $R_4$ is a straight chain alkyl group of 1 to 8 carbon atoms;
   $Q_1$ is a single bond, an ether bond or a —C(=O)—O— ester bond;
   $Q_2$ and $Q_3$ are independently a carboxylic acid ester bond or an ether bond;
M is

-[A]-X-[B]-Y-[C]- in which one of X and Y is a single bond, the other is a carboxylic acid ester bond, and all rings -[A]-, -[B]- and -[C]- are p-phenylene or ring

-[A]- and ring

-[C]- are p-phenylene and ring

-[B]- is 2,5-pyrimidinediyl and X and Y are a single bond or M is

-[A]-X-[B]- in which X is a single bond, and both of rings

-[A]- and -[B]- are p-phenylene; and
   the carbon atoms with the asterisk (*) denote asymmetric carbon atoms.

2. An optically active compound according to claim 1 in which $R_2$ and $R_3$ are methyl.

3. Optically active compounds according to claim 1, wherein M is

-[A]-X-[B]-;

X is a single bond; both of

-[A]- and -[B]- are p-phenylene.

4. An optically active compound according to claim 1, wherein $R_1$ is an alkyl group of 3–14 carbon atoms; $R_2$ and $R_3$ are methyl; $R_4$ is an alkyl group of 3 to 4 carbon atoms; $Q_1$ and $Q_2$ are an ether group, $Q_3$ is an ether group or a carboxylic acid ester group.

5. An optically active compound according to claim 4, wherein $R_1$ is n—$C_8H_{17}$, and X is a carboxylic acid ester group, and Y is a single bond.

6. An optically active compound according to claim 5, wherein said optically active compound is one selected from the group consisting of $$n\text{-}C_8H_{17}O-\underset{}{\phantom{O}}-O-\overset{O}{\underset{\|}{C}}-\underset{}{\phantom{O}}-\underset{}{\phantom{O}}-O-\overset{(R)}{\underset{CH_3}{\overset{*}{C}H}}-CH_2-CH_2-\overset{(S)}{\underset{CH_3}{\overset{*}{C}H}}-O-Bu,$$

$$n\text{-}C_8H_{17}O-\underset{}{\phantom{O}}-O-\overset{O}{\underset{\|}{C}}-\underset{}{\phantom{O}}-\underset{}{\phantom{O}}-O-\overset{(R)}{\underset{CH_3}{\overset{*}{C}H}}-CH_2-CH_2-\overset{(S)}{\underset{CH_3}{\overset{*}{C}H}}-O-Pr$$

and
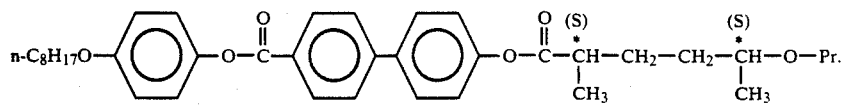
7. An optically active compound according to claim 6, wherein said optically active compound is
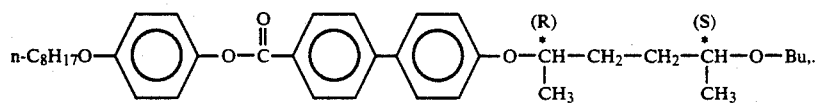
8. An optically active compound according to claim 4, wherein $R_1$ is n—$C_8H_{17}$ and X is a single bond and Y is a thiocarboxylic acid ester group.
9. An optically active compound according to claim 8, wherein said active compound is
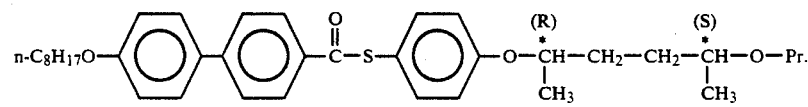
* * * * *